United States Patent [19]

Björklund et al.

[11] 4,092,432

[45] May 30, 1978

[54] MIXTURES HAVING ANTIMICROBIAL OR PESTICIDAL EFFECT

[75] Inventors: Christer James Axel Björklund, Saltsjo-Boo; Alf Ragnar Reuterhäll, Sundsvall, both of Sweden

[73] Assignee: KemaNord AB, Stockholm, Sweden

[21] Appl. No.: 734,927

[22] Filed: Oct. 22, 1976

[30] Foreign Application Priority Data

Oct. 22, 1975 Sweden .............................. 7511852

[51] Int. Cl.$^2$ ................. A61K 31/155; C07C 129/08; A01N 9/20

[52] U.S. Cl. ................................ 424/326; 260/564 C; 260/501.14; 424/316; 71/121

[58] Field of Search ....................... 260/564 C, 501.14; 424/316, 326; 71/121

[56] References Cited

U.S. PATENT DOCUMENTS

| | | | |
|---|---|---|---|
| 1,737,192 | 11/1929 | Hetn | 260/564 C |
| 2,325,586 | 8/1943 | Bolton et al. | 260/564 C |
| 3,499,927 | 3/1970 | Badcock et al. | 260/564 C |

*Primary Examiner*—Gerald A. Schwartz
*Attorney, Agent, or Firm*—Fred Philpitt

[57] ABSTRACT

The present invention relates to mixtures of guanidated aliphatic polyamines, or their acid addition salts, having antimicrobial or pesticidal effect. More particularly the invention relates to such mixtures which have a total degree of guanidation exceeding 30%. The mixtures are suitable for agricultural and industrial use.

5 Claims, No Drawings

MIXTURES HAVING ANTIMICROBIAL OR PESTICIDAL EFFECT

BACKGROUND

It is previously known that guanidine derivatives of some compounds possess antimicrobial or pesticidal properties. U.S. Pat. No. 2,289,541 describes the utilization of dodecylguanidine acetate and similar compounds as insecticides and in U.S. Pat. No. 2,867,562 states that the same compounds are particularly active against fungi on fruit trees. It is further known from British Pat. No. 1,114,155 that specific guanidated polyamines are used against pathogenic organisms. However, this British Patent relates to polyamines having only the primary amino groups, i.e. the end-groups of the polyamine, quanidated and it is furthermore characteristic of these bis-guanidine derivatives that the two guanidine groups are separated by at least 12 carbon and nitrogen atoms.

THE PRESENT INVENTION

According to the present invention it has surprisingly been found that guanidated polyamines generally have antimicrobial or pesticidal properties quite independent of which nitrogen atoms in the polyamine that have been guanidated. It has also been established that the antimicrobial or pesticidal effect is not dependent on the number of carbon atoms between the guanidine groups in the molecule. Likewise the effect is independent of whether the end-groups of the polyamine are guanidated or are present as free amino groups. This discovery means that antimicrobial or pesticidal polyamine derivatives can be prepared very easily and without demands on specific and selective methods of guanidation in order to secure guanidation of certain of the amino groups in the starting material. As there is no requirement for selective guanidaton, a technical mixture of polyamines can thus be brought to react with an unspecific guanidation reagent, e.g. cyanamide, during such time that the desired degree of guanidation is obtained, without complicated control of the reaction conditions. In order to obtain an antimicrobial or pesticidal effect it seems that is is essential only that a certain degree of guanidation of the polyamide is obtained, namely a degree of guanidation exceeding 30% and preferably exceeding 70%.

As no specific guanidation of certain amino groups is required in order to obtain the desired effect, mixtures of polyamines having varying numbers of alkylene chains can also be used as the starting material, which further simplifies and reduces the cost of the preparation of the mixtures, as no particular fractionation of the starting material is necessary.

The guanidated polyamines in the mixtures are characterized by the general formula

  (1)

wherein X is hydrogen or a carboxamidine group, optionally substituted with alkyl groups having 1 to 4 carbon atoms, $R_1$ and $R_2$, independent of each other, are aliphatic groups having 3 to 14 carbon atoms, whereby the groups $R_2$ may be different with $n > 1$, and where $n = 1-6$, whereby, however, all of the guanidine derivatives in the mixtures do not have two carboxamidine groups in end-position. The amine derivatives of the above formula in the mixtures are, as a result of the basicity of the guanidine groups, generally present as acid addition salts.

Preferably all of the guanidine groups in the mixture are unsubstituted. $R_1$ and $R_2$ are, independent of each other, preferably alkylene groups having 3 to 11 carbon atoms such as propylene, butylene, pentylene, hexylene, heptylene, octylene, nonylene, decylene or undecylene groups or cycloalkylene groups having 5 to 8 carbon atoms such as cyclopentylene, cyclohexylene, cyclohdeptylene or cyclooctylene groups. The groups $R_2$ of the above definition need not necessarily be the same when $n$ is greater than 1. As has been mentioned above, the polyamines are usually present as acid salts and are then salts of mineral acids, e.g. chlorides, sulfates, nitrates, phosphates or salts or organic acids such as formates, acetates, fumerates, stearates, oleates, adipates, benzoates, sulfonates etc. The anions are selected in a known manner according to the field of application of the mixture.

It has surprisingly been found that the mixtures according to the present invention, in which are present polyamines having guanidated primary and secondary amino groups, regardless of the space between adjacent guanidine groups and regardless of conformity between the guanidated polyamines in the mixtures, have good antimicrobial or pesticidal properties.

The mixtures of the present invention are characterized by a total degree of guanidation exceeding 30%. A degree of guanidation exceeding 30% for the mixtures means according to the present invention that the total number of carboxamidine groups in a mixture of guanidine derivatives of formula (1) exceeds 30% of the total number of nitrogen atoms based on the mixture of compounds of formula (1) or acid addition salts thereof, whereby nitrogen atoms in the carboxamidine groups are thus not included. The degree of guanidation is most preferably 70-95%.

A particular advantage of mixtures having a high degree of guanidation is the efficacious utilization of the amino groups of the polyamines. At degrees of guanidation exceeding 70% the polyamines are effectively utilized which results in a substantial economic improvement as the raw material costs are reduced. As an example it can be mentioned that at 83% degree of guanidation 24% less of polyamine is required in order to obtain the same pesticidal effect as with the bis-quanidine derivatives described in the British Pat. No 1,114,155.

The mixtures according to the present invention are prepared by guanidation of a mixture of partly neutralized polyamine of the general formula

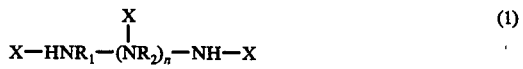

where $R_1$, $R_2$ and $n$ have the previously designated meanings, or a mixture of these, to a degree of guanidation exceeding 30%. The guanidation can be carried out with e.g. cyanamide, urea- or thiourea deriatives in absence of water, in water solution or in a mixture of water and solvent at temperature between 30° and 150° C, preferably between 60° and 100° C. The guanidation reaction is markedly rapid and maximum yield is obtained after a total reaction time of about 5 to 7 hours, including time for charging.

The polyamines from which the mixtures of the invention are prepared are suitably obtained by hydrogenation of nitriles or mixtures of nitriles having chain lengths corresponding to $R_1$ and $R_2$ in formula (1) but with one carbon atoms less. The hydrogenation is carried out at temperatures of about 100°–200° C and in presence of, for example, a nickel catalyst. The hydrogenation is regulated for the formation of primary amines which, in a manner known per se, are di-and oligomeried. After hydrogenation the obtained polyamine mixtures can without preceding separation be directly guanidated in the described manner.

According to a preferred method the mixtures of the present invention are prepared by reacting polyamine acetate having a degree of neutralization of 60–98 and cyanamide in aqueous solution at a temperature of 60°–100° C. After a reaction time of about 5 hours the mixture is obtained in a homonogenous solution, which, after adjusting the pH, is storage stable at −10° C.

In the preparation of the mixtures of the present invention there are no demands on guanidation of specific amino groups in the polyamines. As the mixtures contain randomly guanidated polyamines they can be prepared by a very simple and consequently economical technical process. The preparation of previously known bis-guanidine derivatives for the same fields of application requires low temperature and uneconomically long reaction times, and compared to this the present mixtures can be prepared in maximum yields in a short time and at higher temperature without greater requirements for temperature control.

The mixtures according to the present invention are useful as antimicrobial and pesticidal agents for industrial and agricultural applications, e.g. microbiocides and microbiostatic agents for killing or control of soil fungi and bacteria, and for the protection of seed, fruits, bulbs and plants. It has also been found that the mixtures have a certain growth-regulating effect. They can further be used as algicides in the treatment of pools and reservoirs, as nematocides, insecticides, larvicides and ovicides. Since the mixtures have antimicrobial effect, they can also be used where such an effect is desired relative to animals and man.

The usefulness of the mixtures as antimicrobial agents is not only evident from their activity against bacteria and fungi which arrest growth and even destroys many kinds of crops, but also against those which cause deterioration and degradation of many types of materials. These include paper, timber, leather, textiles, water-containing preparations, such as latex paints, binders, resins, pigment dispersions and coatings based on turpentine balsam, which are particularly liable to be destroyed by fungi. The great economic losses which occur in the production of paper caused by accumulation of slime from bacterial and fungi in different parts of the system can to a considerable extent be eliminated by the use of the present mixtures. In agriculture there are serious problems in the cultivation of wheat, rye, rice, sugar-cane, beets, strawberries and different kinds of crops due to the harvest loss per area unit caused by different soil- and seed-borne fungus diseases from fungi such as Fusarium, Helminthosporium and Septoria species. An excellent control and elimination of these losses has to a great extent been achieved by utilization of the herein described mixtures in a manner known per se for each crop. They can also be used on foliage and trees for control of bacteria and fungi diseases. When the mixtures are used as e.g. seed-dressing agents, a further advantage is obtained besides the fungicidal effect, as it has been found that the mixtures act as bird-repellants, probably due to their bitter taste.

The mixtures according to the present invention are particularly useful as fungicides for horticultural and agricultural applications. A preferred mixture for this use has a degree of guanidation between 70 and 95% and contain guanidated dioctylene triamines and guanidated trioctylene tetraamines. For these uses the mixtures can be included in formulations known per se in concentrations between 1 to 60 % by weight. Solid preparations such as wettable powders, granules and pellets comprise diluents such as talc, clay, silicates, kaolin, etc. Liquid preparations contain water or solvents such as ethanol, ethyl acetate, ethyl cellosolve, ethylene glycol, propylene glycol, vegetable oils, dimethyl formamide, dimethyl sulfoxide, N-methylpyrrolidone etc., or mixtures of water and solvents of the mentioned kind. In a seed-dressing test with the mixtures they have shown good effect against fungi such as Fusarium, Tilletia and Septoria, as well as low phytotoxicity.

Compositions of the mixtures containing known diluents and formulation additives of above mentioned types are thus also within the scope of the present invention.

It is also within the scope of the present invention that these compositions can contain other known antimicrobial or pesticidal substances.

The invention is further illustrated by the following examples, which, however, are not intended to limit the scope of the invention.

EXAMPLE 1

Preparation of triacetate of guanidated 1,13-diamino-7-azatridecane 1,13-diamino-7-azatridecane (110 g) was dissolved during partial neutralization in water (250 g) containing acetic acid (74 g). The mixture was warmed (75° C) and the cyanamide solution (50 %, 154 g) was added during agitation (2 hours). The reaction mixture was then allowed to react further (75° C, 5 h). The solution was neutralized with acetic acid (about 18 g). The product was isolated as a yellow-brown syrup after partial evaporation. The obtained mixture had a degree of guanidation of 92 %.

EXAMPLE 2

Preparation of tetraacetate of guanidated 1,20-diamino-4,17-diazaeicosane 1,20-diamino-4,17-diazaeicosane (157 g) is dissolved during partial neutralization in water (300 g) containing acetic acid (95 g). The mixture is warmed (75° C) and cyanamide solution (50 %, 200 g) is added during agitation (2 hours). The reaction mixture is then allowed to react further (75° C, 5 hours). The solution is neutralized with acetic acid (about 25 g). The product is isolated as a yellow-brown syrup after evaporation. The product has a degree of guanidation of 88 %.

EXAMPLE 3

Preparation of tetraacetate of guanidated 1,4-bis-(5-amino-2-azapentyl)-cyclohexane 1,4-bis-(5-amino-2-azapentyl)-cyclohexane (130 g) is dissolved during partial neutralization in water (250 g) containing acetic acid (98 g). The mixture is warmed (75° C) and cyanamide solution 50 %, 215 g) is added during agitation (2 hours) whereafter the mixture is further reacted (75° C, 2 hours). The solution is neutralized with acetic acid (about 24 g) and partially evaporated. The product was isolated as a yellowish syrup. The obtained mixture had a degree of guanidation of 95 %.

EXAMPLE 4

Preparation of triacetate of guanidated technical 1,17-diamino-9-azaheptadecane 1,17-diamino-9-diazaheptadecane (130 g) is dissolved during partial neutralization in water (100 g) containing acetic acid (59 g) and warmed (75° C). Cyanamide solution (51 %, 56 g) is added (5 hours) during agitation, whereafter the mixture is allowed to react further (2 hours). The solution is neutralized with acetic acid (about 15 g) and the degree of guanidation of the obtained mixture was determined to 45.0 %.

EXAMPLE 5

Preparation of tetraacetate of guanidated technical 1,14-diamino-4,11-diazatetradecane Technical 1,14-diamino-4,11-diazatetradecane, also containing higher oligomers of this tetraamine, (100 g) is dissolved during partial neutralization in water (100 g) containing acetic acid (140 g). The mixture is warmed to 70° C and cyanamide solution (45 %, 171 g) is added (4.5 hours). After a reaction time of 3.5 hours the reaction mixture is neutralized with acetic acid (about 25 g). The guanidation degree is determined to 85.9 %. The degree of guanidation for primary amino groups is determined to 88.7 % and for secondary amino groups to 81.4, i.e. the selectivity is in this case somewhat greater for guanidation of primary amino groups.

EXAMPLE 6

Preparation of triacetae of guanidated 1,7-diamino-4-azaheptane 1,7-diamino-4-azaheptane (130 g) is dissolved during partial neutralization in water (130 g) containing acetic acid (143 g). The mixture is warmed (70° C) and cyanamide solution (50 %, 300 g) is added (5 hours) during agitation, whereafter the mixture is allowed to react further (3 hours). pH is adjusted to 6.5 with acetic acid (about 40 g). The degree of guanidation is determined to 85.4 %. The degree of guanidation for primary amino groups is 81.4 % and for secondary amino groups 93.9 %, i.e. the selectivity is in this case somewhat higher for guanidation of secondary amino groups.

EXAMPLE 7

Preparation of triacetate of guanidated technical 1,17-diamino-9-azaheptadecane

Technical 1,17-diamino-9-azaheptadecane containing 1,8-diamino-octane and higher oligomers thereof (3650 kg) was charged to a reactor containing water (9350 kg) and acetic acid (1720 kg) and warmed to 70° C whereby cyanamide solution (50.7%, 3040 kg) was charged (5 hours). The mixture is allowed to react further (2 hours) whereafter the mixture is neutralized with acetic acid (1000 kg). The degree of guanidation is determined to 87.2%.

EXAMPLE 8

Growth tests were carried out according to the Hiltner method, which means that infected oats, not dressed and dressed according to what is said below, were allowed to grow in plates containing moist brick gravel at 13°-14° C and about 80% relative humidity. The tests lasted 3 months whereafter the number of infected plants were determined and the degree of germination was calculated. Every test was carried out with 300 grains.

Wheat infected with both Fusarium nivale and Septoria nodorum and rye infected with Fusarium nivale were used at the tests. The dressing was carried out by intimate mixing of the grains with the seed-dressing formulations whereafter the grains were allowed to be in contact with the formulations for 24 hours before the growth.

The following seed-dressing agents were used in formulations containing 20% of ethylene glycol:

A = a mixture having a degree of guanidation of 45% containing guanidated dioctylene triamines
B = Bis-(8-guanidinooctyl)-amine according to the British patent 1,114,155, degree of guanidation 67%.
C = a mixture having a degree of guanidation of 83% containing guanidated dioctylene triamines.

The results are shown in the table below.

TABLE

| Seed-dressing agent | % amine | Degree of guanidation % | Relative amine consumption | Dose ml/kg grains | Effect (0 days – 3 months) | | | |
|---|---|---|---|---|---|---|---|---|
| | | | | | Wheat | | Rye | |
| | | | | | Infected | Germination % | Infected | Germination % |
| Not dressed | — | — | — | 2 | 61–63 | 95–96 | 84–72 | 74–84 |
| A | 26.4 | 45 | 1.85 | 2 | 1–1 | 96–96 | 1–3 | 89–82 |
| B | 17.8 | 67 | 1.25 | 2 | 0–0 | 96–95 | 0–1 | 91–91 |
| C | 14.3 | 83 | 1.0 | 2 | 0–1 | 97–95 | 0–0 | 90–89 |

We claim:
1. Mixtures of guanidated aliphatic polyamines having the general formula

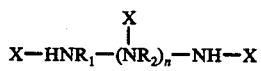

or their acid addition salts, wherein X is hydrogen or a carboxamidine group, optionally substituted with alkyl groups having 1 to 4 carbon atoms, $R_1$ and $R_2$ independent of each other are aliphatic groups having 3 to 14 carbon atoms, whereby the groups $R_2$ may be different when $n > 1$, and where $n = 1$–6, said mixtures having an antimicrobial or pesticidal effect and being characterized in that they have a total degree of guanidation between 70 and 95%.

2. Mixtures of randomly guanidated aliphatic polyamines having the general formula

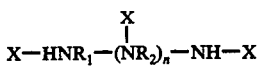

or their acid addition salts, wherein X is hydrogen or a carboxamidine group, optionally substituted with alkyl groups having 1 to 4 carbon atoms, $R_1$ and $R_2$ independent of each other are aliphatic groups having 3 to 14 carbon atoms, whereby the groups $R_2$ may be different when $n>1$, and where $n = 1-6$, said mixtures having antimicrobial or pesticidal effect and being characterized in that they have a total degree of guanidation exceeding 30% and in that not all of the guanidine derivatives in the mixtures have two carboxamidine groups in end-position.

3. Mixtures according to claim 2 characterized in that they have a degree of guanidation exceeding 70%.

4. Antimicrobial or pesticidal compositions containing 1 to 60 percent by weight of mixtures according to claim 2 and diluents known per se.

5. A process for treating materials or hosts containing microbes, fungi or pests which comprises applying thereto an amount of a mixture set forth in claim 2 which will be effective to reduce the number of said microbes, fungi or pests.

* * * * *